(12) United States Patent
Wu et al.

(10) Patent No.: US 11,633,276 B2
(45) Date of Patent: Apr. 25, 2023

(54) IOL FOLDING DEVICE

(71) Applicant: Alcon Inc., Fribourg (CH)

(72) Inventors: Yinghui Wu, Cedar Hill, TX (US); Douglas Brent Wensrich, Bedford, TX (US); Todd Taber, Keller, TX (US); Len Takudzwa Magara, Pretoria (CA)

(73) Assignee: Alcon Inc., Fribourg (SE)

( * ) Notice: Subject to any disclaimer, the term of this patent is extended or adjusted under 35 U.S.C. 154(b) by 838 days.

(21) Appl. No.: 16/454,460

(22) Filed: Jun. 27, 2019

(65) Prior Publication Data

US 2020/0197168 A1 Jun. 25, 2020

Related U.S. Application Data

(60) Provisional application No. 62/781,862, filed on Dec. 19, 2018.

(51) Int. Cl.
*A61F 2/16* (2006.01)

(52) U.S. Cl.
CPC .......... *A61F 2/1678* (2013.01); *A61F 2/167* (2013.01); *A61F 2/1691* (2013.01); *A61F 2002/1681* (2013.01)

(58) Field of Classification Search
CPC ...... A61F 2/1678; A61F 2/167; A61F 2/1691; A61F 2002/1681
See application file for complete search history.

(56) References Cited

U.S. PATENT DOCUMENTS

| 6,858,033 | B2 * | 2/2005 | Kobayashi | ............ | A61F 2/1678 |
| | | | | | 623/6.11 |
| 2009/0043313 | A1 * | 2/2009 | Ichinohe | ............... | A61F 2/1678 |
| | | | | | 606/107 |
| 2021/0059811 | A1 * | 3/2021 | Hangya | ................. | A61F 2/1691 |

FOREIGN PATENT DOCUMENTS

| EP | 1360944 A2 | 11/2003 | | |
| WO | 2015070994 A1 | 5/2015 | | |
| WO | WO-2015112144 A1 * | 7/2015 | ........... | A61F 2/1678 |

* cited by examiner

*Primary Examiner* — Richard G Louis
*Assistant Examiner* — Chima U Igboko
(74) *Attorney, Agent, or Firm* — Patterson + Sheridan, LLP

(57) ABSTRACT

An intraocular lens (IOL) folding device is described.

12 Claims, 13 Drawing Sheets

IOL FOLDING DEVICE

CROSS-REFERENCE TO RELATED APPLICATIONS

This application claims priority to U.S. Provisional Application Ser. No. 62/781,862, filed on Dec. 19, 2018, the contents of which is incorporated herein by reference in its entirety.

TECHNICAL FIELD

The present disclosure relates to systems, apparatuses, and methods for intraocular lens (IOL) injectors.

BACKGROUND

The human eye in its simplest terms functions to provide vision by transmitting and refracting light through a clear outer portion called the cornea, and further focusing the image by way of the lens onto the retina at the back of the eye. The quality of the focused image depends on many factors including the size, shape, and length of the eye, and the shape and transparency of the cornea and lens. When trauma, age, or disease cause the lens to become less transparent, vision deteriorates because of the diminished light which can be transmitted to the retina. This deficiency in the lens of the eye is medically known as a cataract. The treatment for this condition is surgical removal of the lens and implantation of an artificial lens (IOL).

Many cataractous lenses are removed by a surgical technique called phacoemulsification. During this procedure, an opening is made in the anterior capsule of an eye and a phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced with an IOL.

The IOL may be injected into the eye through a small incision, sometimes the same incision used to remove the diseased lens. An IOL injector may be used to deliver an IOL into the eye.

SUMMARY

An intraocular lens (IOL) folding device is described. The IOL folding device has a housing, a pair of IOL storage shelves disposed within opposite sides of the housing, each IOL storage shelf adapted to support a portion of an unfolded IOL. The IOL folding device also has an IOL folding channel formed between the IOL storage shelves, each IOL storage shelf coupled to the IOL folding channel by a lip, the IOL folding channel having a longitudinal axis adapted to be aligned with a bore of an IOL injector, and having a bottom surface forming a floor. The IOL folding device also has an IOL folding guide axially aligned and above the IOL folding channel, the IOL folding guide having a first end adapted to contact an upper surface of an IOL and a second end coupled to the housing or a user-actuatable handle. The user-actuatable handle has a first end accessible to a user and a second end coupled to the IOL folding guide or the IOL folding channel. In response to actuation of the lever or button, the floor of the IOL folding channel and the IOL folding guide are adapted to be brought closer together, the IOL folding guide thereby configured to push an unfolded IOL into the IOL folding channel and adopt a folded conformation within the IOL folding channel.

The IOL folding channel may be disposed within a block, the block coupled to and slidably movable within the housing. The user-actuatable handle may include a lever having a first end accessible to a user and a second end coupled to the block, and the IOL folding device may include a spring having a first end coupled to the block and a second end coupled to the housing. In response to actuation of the lever, the block may be adapted to move from a resting position wherein the channel is aligned with the bore, such that the floor of the IOL folding channel moves towards the IOL folding guide, thereby pushing the IOL into the IOL folding channel. The spring may be adapted to return the block to the resting position.

The IOL folding guide may include a first and a second arm, each arm having a first end and a second end, wherein an inner hook is disposed on the first end, the inner hook adapted to contact an inner edge of an IOL base.

The IOL folding guide may include a first and a second arm, each arm having a first end and a second end, wherein an outer hook is disposed on the first end, the outer hook adapted to contact an outer edge of a haptic.

The IOL may have an IOL base comprising proximal and distal notches disposed within the inner edge of the IOL base, and the inner hooks may be adapted to contact the IOL base at the proximal and distal notches.

The IOL folding guide may include a first and a second cam, each cam having a wedge extending therefrom and rotatably coupled to a beam and rotationally movable along a track, the wedges adapted to contact an inner edge of an IOL base. The user-actuatable handle may include a button slidably disposed within a first side of the housing, the button having a first end depressible by a user and a second end coupled to the beam. The IOL folding device may include a spring having a first end coupled to the button and a second end coupled to the housing. In response to depression of the button, the beam may be adapted to move from a resting position toward the floor of the IOL folding channel, the cams may be adapted to rotate along the tracks, the wedges may be adapted to contact the IOL base and thereby push the IOL into the IOL folding channel and axially elongate the IOL base, and the spring may be adapted to return the button to the resting position.

The IOL base may include proximal and distal notches disposed within the inner edge of the IOL base, and the wedges may be adapted to contact the IOL base at the proximal and distal notches.

The IOL folding guide may include a first and a second flexible arm, each flexible arm having a first end and a second end, wherein an inner hook is formed on a first end, the inner hook adapted to contact an inner edge of an IOL base. The IOL folding device may include a user-actuatable handle having a button slidably disposed within a first side of the housing, the button having a first end depressible by a user, and a second end coupled to the second end of the flexible arms, and a spring having a first end coupled to the button and a second end coupled to the housing. In response to depression of the button, the flexible arms may be adapted to move from a resting position toward the floor of the IOL folding channel, the flexible arms may be adapted to flex axially in response to resistance of an unfolded IOL base adopting a folded configuration as the IOL base enters the IOL folding channel, such that the first ends of the flexible arms move away from each other, the inner hooks may be adapted to contact the IOL base and axially elongate the IOL base, and the spring may be adapted to return the button to the resting position.

The first end of each of the flexible arms may include an outer hook adapted to contact an outer edge of a haptic. In response to the axially elongation of the IOL base, the outer hook may be adapted to keep an inner edge of the haptic in contact with an outer edge of the IOL base.

The IOL base may include proximal and distal notches disposed within the inner edge of the IOL base, and the inner hooks may be adapted to contact the IOL base at the proximal and distal notches.

The IOL folding guide may include a beam having a first end and a second end, the beam adapted to contact an upper surface of an IOL. The user-actuatable handle may include a button slidably disposed within a first side of the housing, the button having a first end depressible by a user and a second end coupled to the beam, and the IOL folding device may include a spring having a first end coupled to the button and a second end coupled to the housing. In response to depression of the button, the beam may be adapted to move from a resting position toward the floor of the IOL folding channel, and thereby push the IOL into the IOL folding channel, and the spring may be adapted to return the button to the resting position.

The first end of the beam may include an outer hook adapted to contact an outer edge of a haptic. In response to the beam pushing the IOL into the IOL folding channel, the outer hooks may be adapted to keep the haptics in contact with an outer edge of the IOL base or an IOL optic.

The lip of each shelf may include an overhang extending from the shelves partially over the IOL folding channel, wherein the overhang is configured to retain a folded IOL within the IOL folding channel.

The IOL folding device may be fixedly disposed within or removably disposed within an IOL injector.

The IOL injector may include an injector body having a main body having a proximal end and a distal end, and a nozzle having a proximal end and a distal end, the proximal end of the nozzle coupled to the distal end of the main body. The nozzle may include an IOL storage location configured to house an unfolded IOL, and an IOL dwell location distal to the IOL storage location. The injector body may include a bore having a longitudinal axis extending from the proximal end of the main body to the distal end of the nozzle. A distal portion of the bore within the nozzle may form a delivery channel. The IOL injector may also include a plunger movably coupled within the injector body and aligned within the bore, the plunger having a plunger tip adapted to contact an IOL.

The IOL folding device may be disposed within the nozzle.

The IOL folding device may be disposed within the IOL housing location.

The IOL folding device may be configured such that the plunger is axially movable through the IOL folding channel.

The IOL folding device may be adapted to separately fold an IOL base, an IOL optic, or both.

The IOL folding device may be adapted to concurrently fold an IOL base and an IOL optic.

The floor may be configured to be beneath a centroid of an unfolded IOL when the unfolded IOL is positioned on the shelves.

BRIEF DESCRIPTION OF THE DRAWINGS

For a more complete understanding of the present disclosure, reference is now made to the following description, taken in conjunction with the accompanying drawings, which are not to scale, and in which.

DETAILED DESCRIPTION

Figure 1:
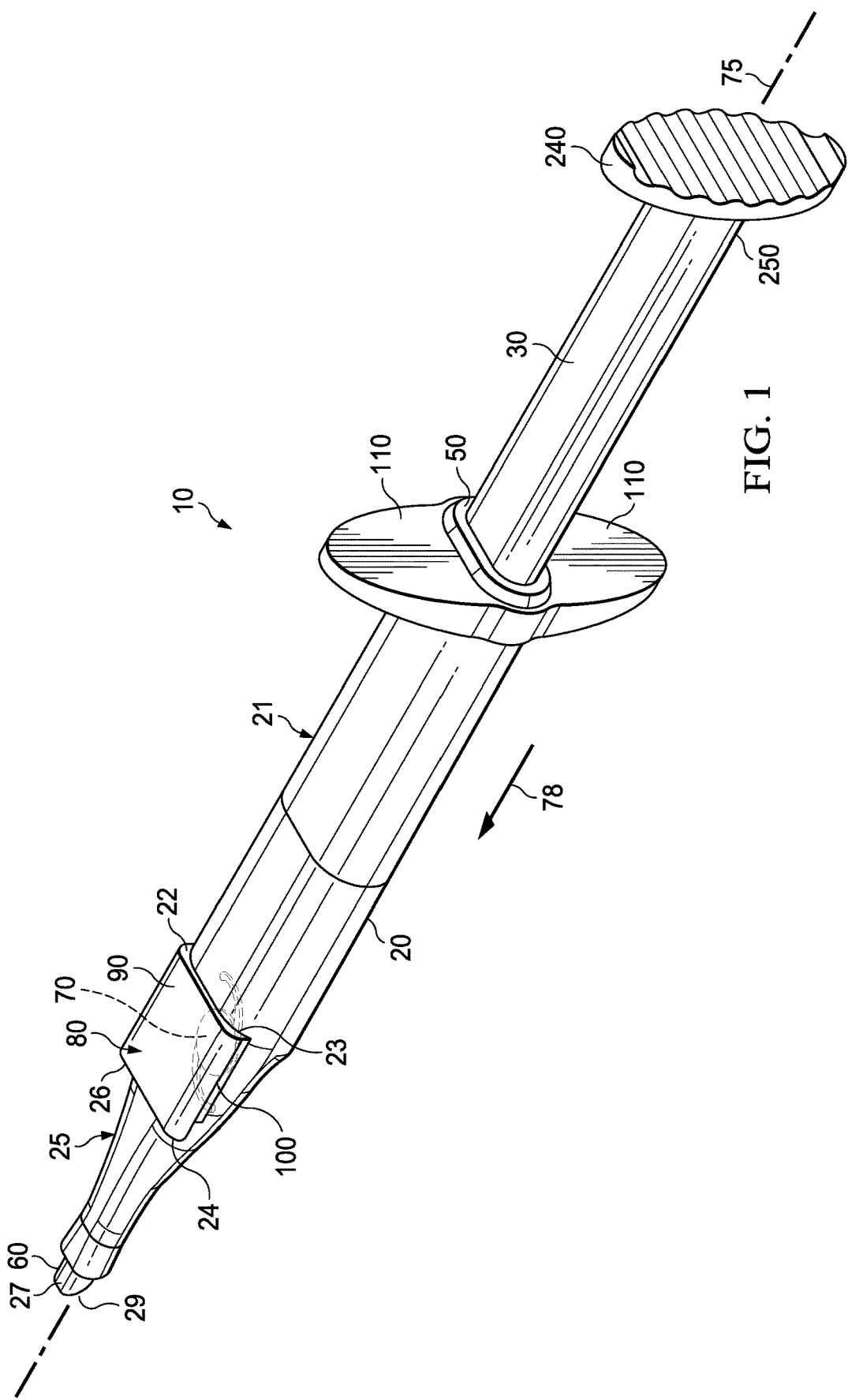
FIG. 1 is a perspective view of an example IOL injector.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Figure 2:
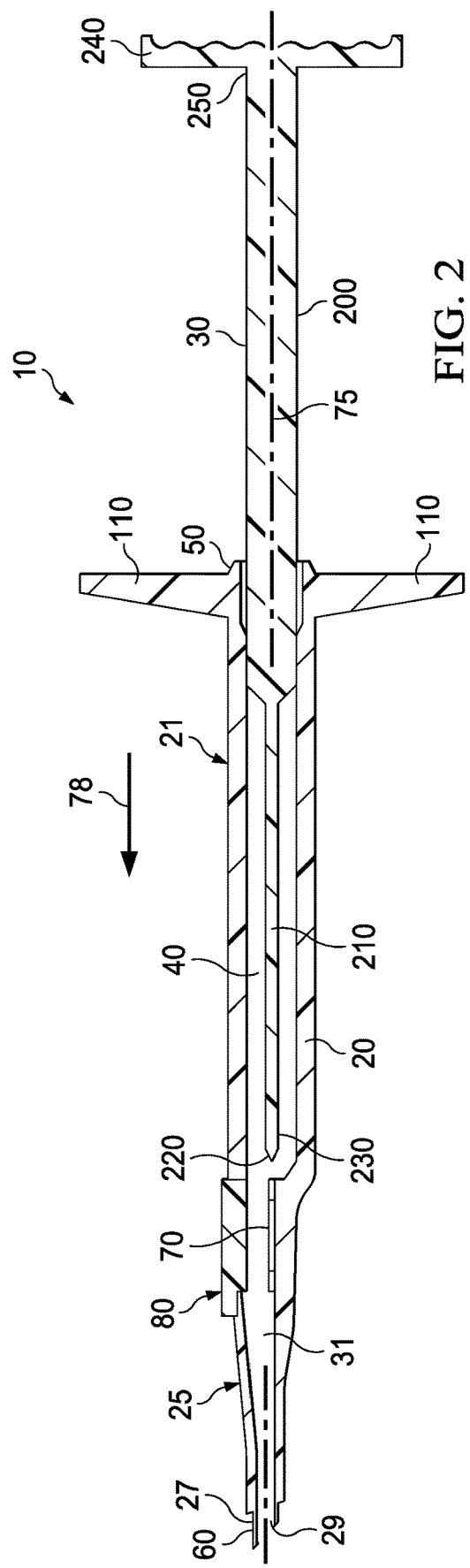
FIG. 2 is a longitudinal cross-sectional view of the example IOL injector of FIG. 1.

FIGS. 1 and 2 are schematics of an example IOL injector 10 that is actuated by manual user application of force. The IOL injector 10 includes an injector body 20, a plunger 30 adapted to reciprocate through a bore 40 formed in the injector body 20. The injector body 20 has a main body 21 having a proximal end 50 and a distal end 23, and a nozzle 25 having a proximal end 22 and a distal end 60. The proximal end 22 of the nozzle 25 is coupled to the distal end 23 of the main body 21. The nozzle 25 has an IOL storage location 80 configured to house an uncompressed and unfolded IOL 70.

The bore 40 extends from the proximal end 50 of the main body 21 to the distal end 60 of the nozzle 25. A distal portion of the bore 40 within the nozzle 25 forms a tapered delivery channel 31 through which an IOL may be axially advanced, compressed, and delivered into an eye via an opening 29 in distal tip 27 at distal end 60.

The plunger 30 is movably coupled within the injector body 20 and aligned within the bore 40. The plunger 30 has a plunger tip 220 adapted to contact an IOL 70.

The IOL injector 10 also includes a longitudinal axis 75. The longitudinal axis 75 may extend along the plunger 30 and define a longitudinal axis of the plunger 30.

The IOL storage location 80 may include a door 90 to provide access to the interior of the IOL storage location 80.

The door 90 may include a hinge 100 such that the door 90 may be pivoted about the hinge 100 to open the IOL storage location 80 and, for example, allow the installation of the IOL 70. In other implementations, the IOL storage location 80 may exclude a door for installing the IOL 70. In such instances, the IOL 70 may be incorporated into the IOL storage location 80 at the time of assembly of the IOL injector 10. Thus, in such instances, the IOL injector 10 may be a preloaded IOL injector. In such instances, the IOL storage location 80 may have a cover that is not configured to open, rather than a door 90. The IOL storage location 80 may include a hole adapted to allow addition of viscoelastic into the IOL storage location 80.

The injector body 20 may also include tabs 110 formed at the proximal end 50 of the injector body 20. The tabs 110 may be manipulated by fingers, thumb, or hand of a user, such as an ophthalmologist, an ophthalmic surgical assistant or nurse, or other medical professional, to advance the plunger 30 through the bore 40.

The plunger 30 may include a plunger body 200, a plunger rod 210 extending distally from the plunger body 200, and a plunger tip 220 formed at the distal end 230 of the plunger rod 210 and adapted to contact an IOL disposed, for example, with the IOL storage location 80 of the IOL injector 10. As the plunger 30 is axially advanced and thereby displaced distally within the bore 40 in the direction of the arrow 78, the plunger tip 220 of the plunger 30 is adapted to engage and advance the IOL, such as IOL 70. In FIGS. 1 and 2, the IOL 70 is shown located within the IOL storage location 80. The plunger 30 may also include flanges 240 formed at proximal end 250, which may be manipulated by the fingers, thumb, or hand of a user to advance the plunger 30 through the bore 40 by displacing the plunger 30 through the bore 40 distally in the direction of the arrow 78.

Figure 3A:
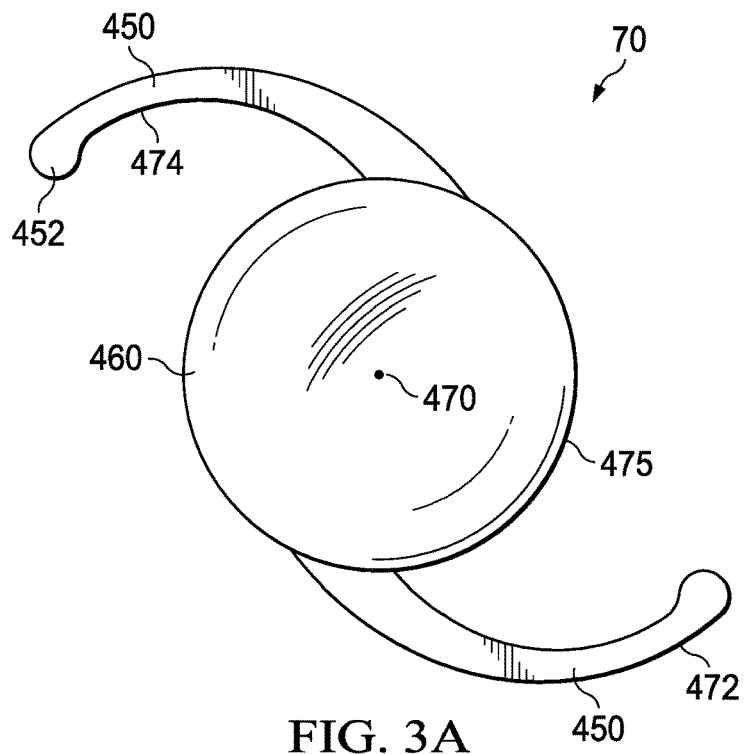
FIG. 3A shows an example one-piece IOL.

In some implementations, the IOL 70 may be a one-piece IOL. That is, in some implementations, the IOL 70 may include an optic 460 and haptics 450, as shown in FIG. 3A. Each of the haptics 450 include a tip 452. In some implementations, the optic 460 and the haptics 450 may be integrally formed out of a single piece of material. In other implementations, the optic 460 may be formed out of one piece of material; the haptics 450 may be formed out of another piece of material, and the optic 460; and the haptics 450 may be coupled together prior to delivery into an eye. In some instances, the optic 460 and haptics 450 may be fixedly secured to each other prior to insertion into an IOL injector and delivered into an eye.

Figure 3B:
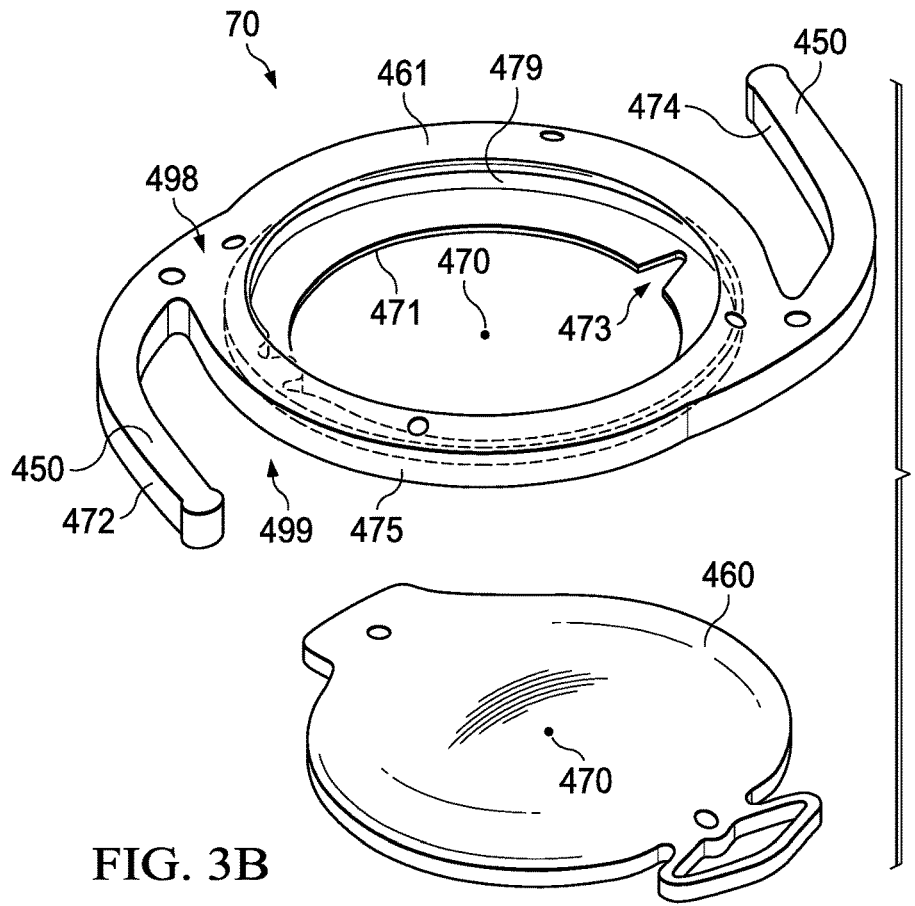
FIG. 3B shows an example two-piece IOL including a base and an optic.

In other implementations, the IOL 70 may be a multi-piece IOL, as shown, for example, in FIG. 3B. For example, in some implementations, the IOL 70 be include two or more separate components. FIG. 3B is an example IOL 70 that includes two removably attached components. As shown in FIG. 3B, the IOL 70 includes an optic 460 and a hollow ring forming a base 461 that includes haptics 450 and that has a top 498 and a bottom 499. The optic 460 and the base 461 are adapted to be coupled together to form a unitary IOL. For example, in some instances, the optic 460 and the base 461 are adapted to be coupled together to form a unitary IOL such as prior to implant, or after implant inside an eye. In some instances, the optic 460 can be detached from the base 461 and be replaced, if desired. In some instances, one or more components of a multi-piece IOL, such as, for example the two-piece IOL 70 shown in FIG. 3B, are separately injectable into a patient's eye. Once in the eye, the components may be assembled into a complete IOL. For example, in the case of the two-piece IOL 70 shown in FIG. 3B, the optic 460 and the base 461 are separately injectable into an eye. Once injected, the optic 460 is adapted to be coupled to the base 461 within the groove 479 disposed within an inner edge 471 of the base 461. In some instances, one or more notches 15 are disposed within the outer edge 8. The one or more notches 15 may be configured for coupling with the optic 460 and thereby orienting assembly of the optic 460 onto the base 461. The notches 15 may also provide an initiation point for the IOL base 461 to begin folding or adopting a compressed conformation. In particular, in some instances, the notches 15 are disposed within the inner edge 8 such that the IOL base 461 adopts a compressed conformation wherein the distal and proximal haptics 450 are each respectively maintained in a distal and a proximal position within the IOL injector as the IOL base 461 adopts the compressed conformation. In some instances, for example, the base 461 can have two notches 15, disposed on opposite sides within the inner edge 8, for example one notch 15 disposed within the inner edge 8 at a position adjacent to a midpoint of the length of the distal haptic 450 and another notch 15 disposed within the inner edge 8 at a position adjacent to a proximal haptic 450. The notches 15 may have other functionality. For example, in some instances, a user may contact the notches 15 with a surgical instrument in order to manipulate the base 461 position during implantation.

Occasionally, patients may require replacement of an IOL, and a procedure to replace an IOL may result in damage to the eye. With the use of a two-piece IOL, for example, a replacement procedure may involve replacement only of the optic, allowing the base to remain in place within the eye.

As explained above, in some implementations, the IOL 70 may be a two-piece IOL wherein the base 461 and the optic 460 are separately injected into the patient's eye. Accordingly, for two-piece IOLs, the base 461 and the optic 460 may be contained in separate IOL injectors 10 for insertion in the eye. In other implementations, the two components of a two-piece IOL may be inserted into an eye separately using a single IOL injector. For a single piece IOL, the optic 460 and haptics 450 form a unitary IOL and are inserted into an eye simultaneously with the use of a single IOL injector.

Accordingly, in some implementations, a user may place a one-piece IOL into an IOL injector, for example, by loading an IOL into an IOL storage compartment of the IOL injector, such as the IOL storage location 80 of the IOL injector described above. As also explained, the IOL storage location 80 may be accessed via a door, such as the door 90.

In the case of a two-piece IOL, in some implementations, a user may load the base, such as base 461, into an IOL storage compartment of an IOL injector, for example, via a door. The optic such as optic 460, may be introduced into the IOL storage compartment of a separate IOL injector, for example, via a door. In some instances, the IOL storage compartment may be accessed through the door such as door 90.

In some implementations, the IOL 70 may be folded into a compressed or folded configuration. In the case of a two-piece IOL, in some implementations, one or both of the base 461 and the optic 460 may be folded into a compressed or folded configuration.

As would be understood by skilled persons, it is important for IOLs to be stored unfolded so as not to become permanently deformed over time. Accordingly, IOLs are typically not held in a folded condition over a long period of time, such as in storage.

Some existing IOL delivery devices involve a manual folding mechanism in which the user places the base of an IOL into a folding chamber and closes the door. Once the door is closed, its internal features and geometry fold the base. However, the user action of loading and folding the base creates the potential for user errors in loading it correctly into the injector and may not ensure that all components remain sterile during the process.

In some implementations, the IOL may be pre-loaded into the storage compartment of an IOL injector, for example, during manufacturing or otherwise prior to distribution to an end user. Accordingly, for the one-piece IOL, the one-piece IOL may be pre-loaded into the storage compartment an IOL injector prior to receipt by the end user. For a two-piece IOL, the base may be pre-loaded into a storage compartment of one IOL injector, while the optic may be pre-loaded into the IOL storage compartment of another IOL injector. The term "pre-loaded" as used herein means that an IOL, either in a one-piece or multi-piece configuration (including, for example, a two-piece configuration) is loaded into the IOL injector not by a user, but, rather, the IOL is installed in the IOL injector before and is already contained within the IOL injector when the IOL injector is received by the user. The IOL injector(s) may be packaged within sterile packaging when received by a user.

As would be understood by persons of ordinary skill in the art upon reading the present disclosure, an IOL that is pre-loaded into an IOL injector has advantages over manual installation and folding of an IOL into the IOL injector that is performed by a user. For example, as explained above, manual installation and folding of an IOL may allow more opportunity for errors, which have the potential to cause unnecessary secondary manipulation or correction during an already complex procedure. For example, manual installation and folding of an IOL may also introduce the possibility of contamination of the IOL, such as by human error or poor sterile technique. Contamination of the IOL may compromise the sterile environment for the patient and risk infection or other harm to the patient.

Because the IOL base 461 is comprised of a hollow ring and two protruding haptics, the base 461 typically has a more complex center of mass than a one-piece IOL 70. For example, the central axis of a base 461 can change when external forces are applied, which may be associated with increased difficulty in properly folding the base 461. For example, most conventional one-piece IOL injectors advance the IOL by directly applying forces to the edge of the IOL optic or haptic. This technique is not well adapted for a hollow base design because the base may sometimes collapse into a suboptimal configuration if an external force is applied to the edge of the base.

Accordingly, the complex geometry of the two-piece IOL typically requires evenly distributed force application on the hollow ring of the base 461, optionally also including an optic 460. In addition, in some implementations described herein, IOL folding may include application of symmetric opposing forces to assist in folding the haptics 450.

Therefore, the present disclosure provides folding mechanisms that may be compatible with IOLs having a hollow base, and possibly also other multi-part IOLs or conventional single-piece IOLs. The self-contained folding mechanisms described herein may also ensure that the IOL remains sterile and intact until implantation in the patient's eye.

The present disclosure relates to systems, apparatuses, and methods for folding an IOL and delivering the folded IOL into an eye.

In various implementations described herein, the IOL injector 10 includes an IOL folding device adapted to fold an IOL, such as a two-piece IOL or a one-piece IOL. In some implementations described herein, the IOL folding device described herein is adapted to provide optimal folding of the IOL by elongating the hollow ring of the IOL base 461 by applying opposing outward axial forces to an inner edge 471 of the base 461, to maintain more control of the center of mass of the base 461 during folding. In some implementations, the IOL folding device described herein may also be adapted to provide optimal folding of the IOL by keeping the haptics 450 close to or in contact with an outer edge 475 of the base 461 and/or the optic 460. In implementations described herein, the IOL folding device is adapted to provide optimal folding of the IOL by pushing the IOL into a folding channel 2 adapted to be aligned with the bore 40 of an IOL injector 10. Subsequently, after the IOL has adopted a folded conformation, the IOL injector having the IOL folding device is adapted such that the plunger tip 220 may contact the folded IOL 70 and axially advance it to be delivered to an eye of a patient.

FIGS. 4A-7 are schematics of various example implementations of an IOL folding device of the present disclosure that may be incorporated into an IOL injector. In some instances, the IOL folding device may form an integral part of the IOL injector. In other instances, the IOL folding device may be a separate component, such as a detachable component that may be removably connected to an IOL injector.

When the IOL folding device is in an unactuated condition, the IOL folding device may serve as an IOL storage compartment in which an IOL (or component thereof) resides in an unfolded condition. The IOL folding device may be disposed within the IOL storage location 80.

The IOL folding device may be used to fold a one-piece IOL or one or more components of a multi-piece IOL. The IOL (or one or more components thereof) may be manually loaded into the IOL folding device by a user or the IOL (or one or more components thereof) may be pre-loaded during manufacturing or at some other time prior to delivery to a user.

In various implementations, the IOL folding device is contained within an IOL folding device housing 99. The housing 99 may form an integral part of the IOL injector body 20, such as fixedly disposed within and forming an integral part of the nozzle 25, the IOL storage location 80, or the main body 21. In other instances, the IOL folding device may be a separate component contained within the housing 99, such as a detachable component that may be removably connected to an IOL injector. The housing 99 of the IOL folding device may be adapted to be removably disposed within the injector body 20 of the IOL injector 10, such as within the nozzle 25, within the IOL storage location 80, or within the main body 21.

Figure 4A:
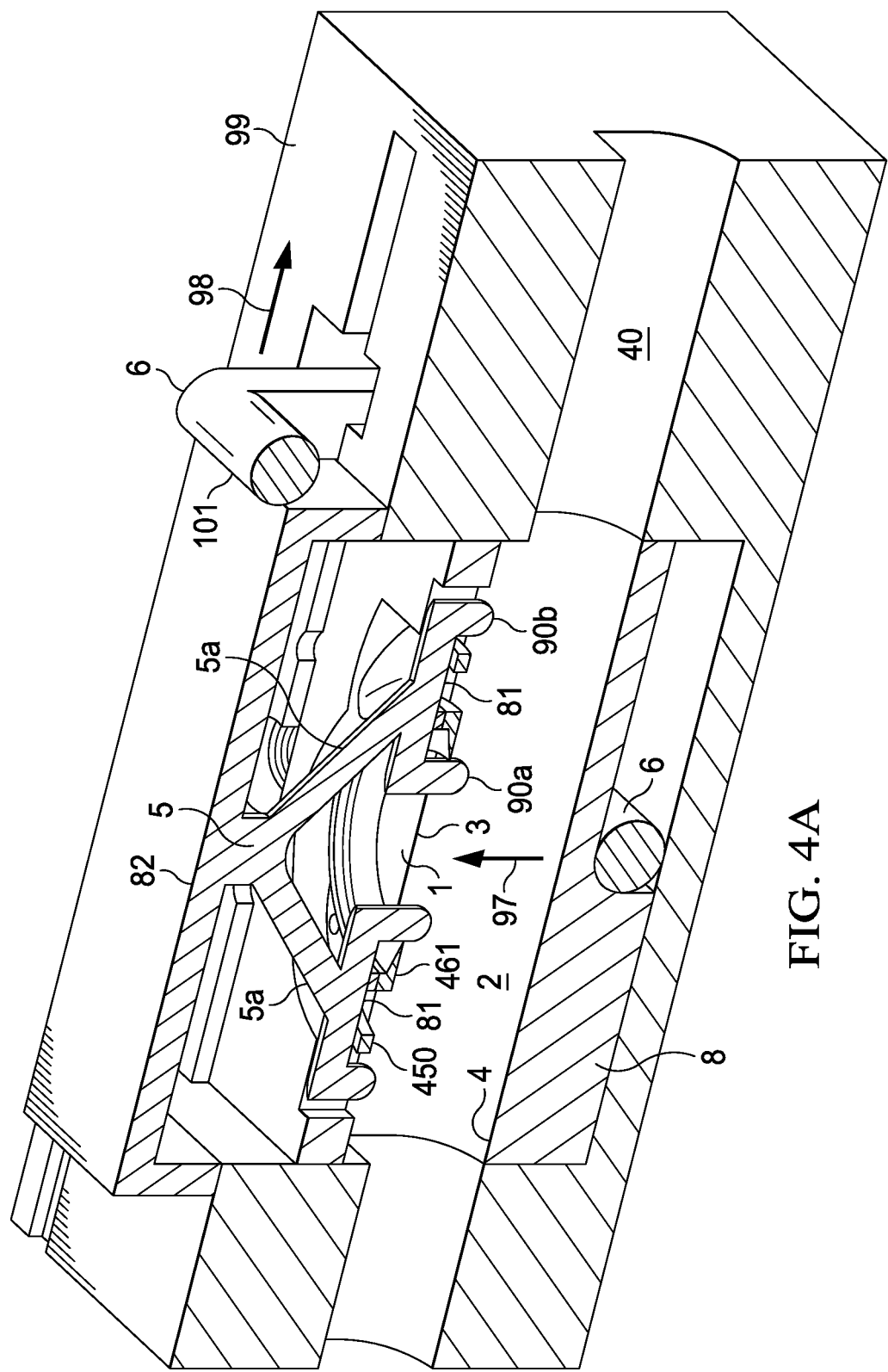
FIG. 4A is a schematic of an example IOL folding device.
Figure 4B:
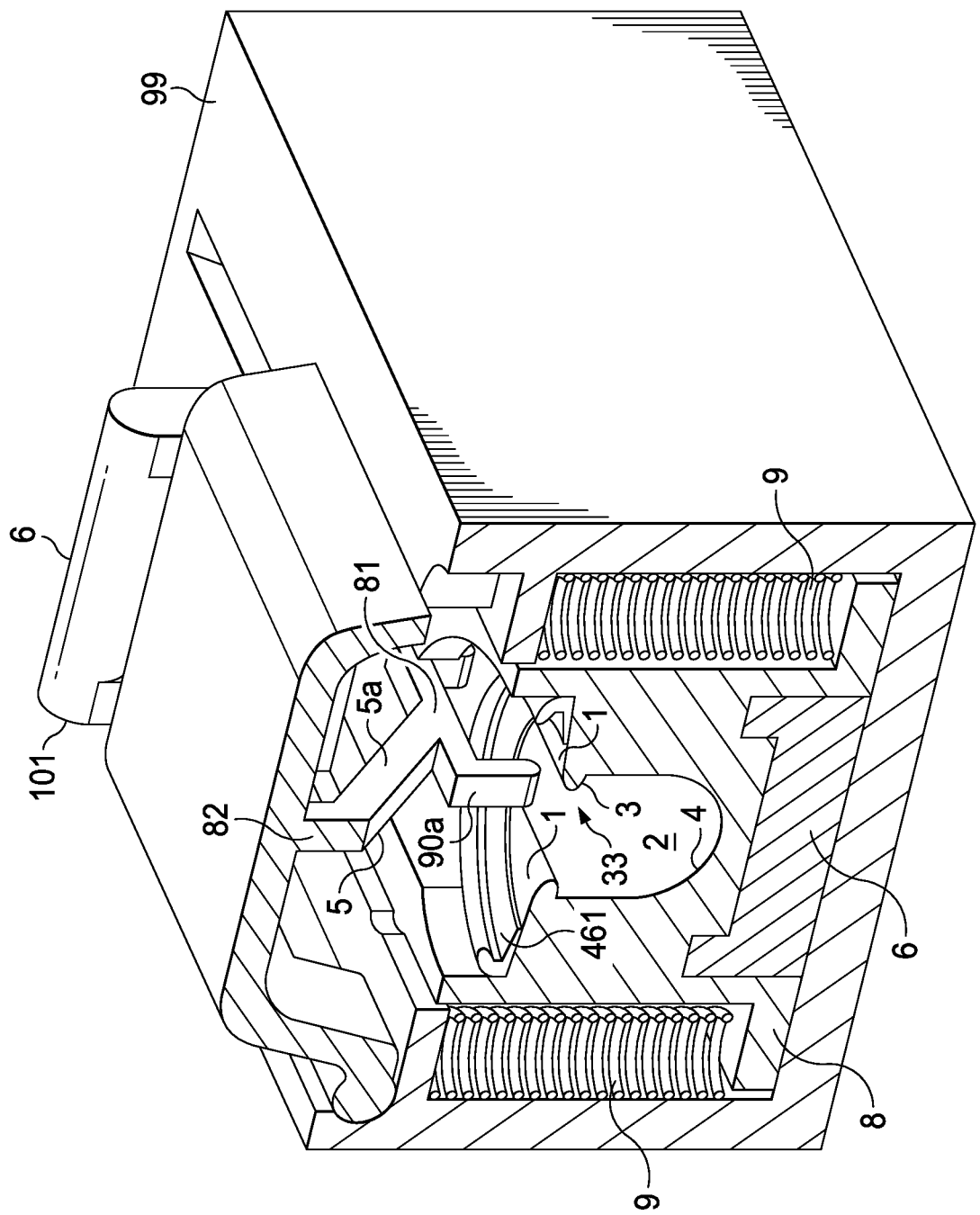
FIG. 4B is another view of the example folding device of FIG. 4A.

The IOL folding device has a pair of IOL storage shelves 1 disposed within laterally opposite sides of the IOL folding device housing 99. For example, FIG. 4A shows a cutaway perspective view of an example IOL folding device, in which the cutaway view is cut along the longitudinal axis and shows only one of the shelves 1, whereas FIG. 4B shows a cutaway perspective view of the same example IOL folding device of FIG. 4A, but with the cutaway view cut laterally and shows both of the shelves 1. When the IOL folding device is integrated within an IOL injector, the pair of IOL storage shelves 1 are disposed within laterally opposite sides of the IOL injector body 20, such as within laterally opposite sides of the IOL storage location 80. Each IOL storage shelf 1 is adapted to support a portion of an unfolded IOL 70. The IOL folding device has an IOL folding channel 2 formed between the IOL storage shelves 1. Each IOL storage shelf 1 is coupled to the IOL folding channel 2 by a lip 3. The IOL folding channel 2 has a longitudinal axis adapted to be aligned with the bore 40 of an IOL injector when the IOL folding device is disposed within an IOL injector body 20. Accordingly, the term "laterally opposite" refers to opposite sides of the IOL folding device that are separated by the IOL folding channel 2. The IOL folding device may include a portion of a bore 40, for example as shown in FIG. 4A, adapted to be axially aligned and coupled with the bore of an IOL injector 10. The IOL folding device has a bottom surface forming a floor 4 configured to be beneath a centroid 470 of an unfolded IOL 70 when the unfolded IOL 70 is positioned on the shelves 1. The term "centroid" as used herein refers to the center of mass of an unfolded IOL 70. Examples of centroids 470 of an unfolded IOL 70, such as a one-piece or two-piece IOL 70 are shown in FIG. 3A and FIG. 3B, respectively. The IOL folding device has an IOL folding guide 5 axially aligned and above the IOL folding channel 2. In various implementations described herein, the IOL folding guide 5 has a first end 81 adapted to contact an upper surface of an IOL 70 and a second end 82 that may be coupled to the IOL folding device housing 99 or a user-actuatable handle 101 such as a user-actuatable lever 6 or a user-actuatable button 7.

In various implementations of the IOL folding device described herein, the user-actuatable lever 6 or button 7 has a first end accessible to a user and a second end coupled to the IOL folding guide 5 and/or the IOL folding channel 2, and configured such that in response to actuation of the lever 6 or button 7, the floor 4 of the IOL folding channel 2 and the IOL folding guide 5 are brought closer together. The IOL folding guide 5 is thereby configured to push an unfolded IOL 70 into the IOL folding channel 2 and in response the IOL 70 adopts a folded conformation within the IOL folding channel 2.

In some implementations, the IOL folding device may be configured such that the lip 3 of each shelf 1 includes an overhang 33 extending from the shelves 1 partially over the IOL folding channel 2, such that the overhang 33 is configured to retain a folded IOL 70 within the IOL folding channel 2.

Figure 4C:
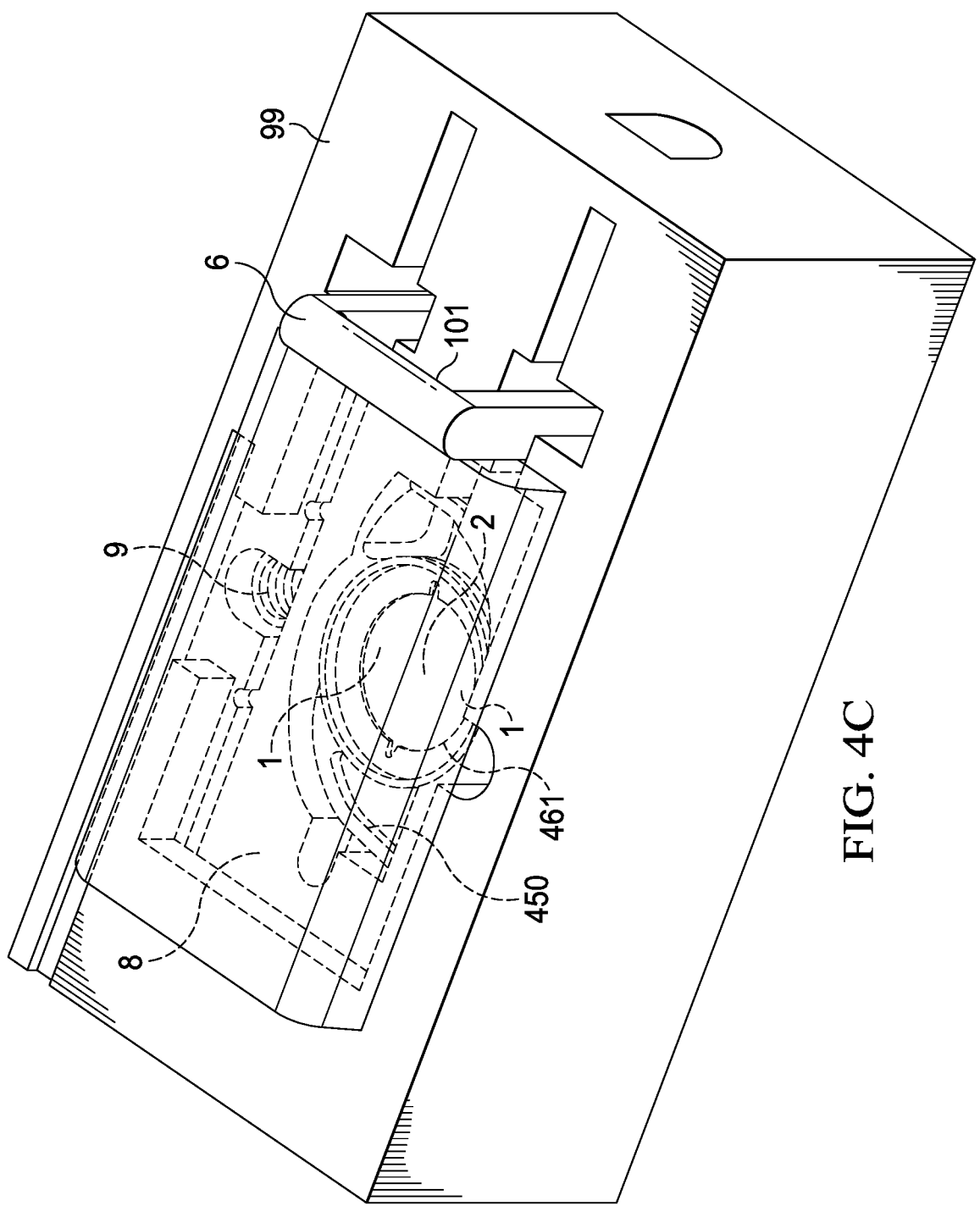
FIG. 4C is another view of the example folding device of FIG. 4A.

FIG. 4A-FIG. 4C are schematics of an example IOL folding device of the present disclosure. In some implementations, such as in the example shown in FIG. 4A-FIG. 4C, the IOL folding channel 2 may be disposed within a block 8 coupled to and slidably movable within the housing 99. The user-actuatable lever 6 may have a first end accessible to a user and a second end coupled to the block 8. The IOL folding device may further include a spring 9 having a first end coupled to the block 8 and a second end coupled to the housing 99. In response to user actuation of the lever 6, for example as shown in the direction of arrow 98 in FIG. 4A, the block 8 is adapted to move from a resting position, for example as shown in the direction of arrow 97 in FIG. 4A, such that the floor 4 of the IOL folding channel 2 moves towards the IOL folding guide 5. Accordingly, the first end 81 of the folding guide 5 then becomes disposed within the folding channel 2, thereby pushing the IOL 70 into the IOL folding channel 2, The resting position may be a position in which the folding channel 2 is aligned with the bore 40 of an IOL injector. The spring 9 is adapted to return the block S to the resting position. In some implementations, the IOL folding device may include a compression spring adapted to return the block 8 to the resting position, for example as shown in FIG. 4A-FIG. 4C, or it may include any other type of spring adapted to return the block 8 to the resting position, such as a tension spring or a torsion spring, among others.

Upon returning to the resting position, the folding channel 2 is adapted to be realigned with the bore 40, and as the folding channel 2 returns to the resting position, the first end 81 of the folding guide 5 exits the folding channel 2. Accordingly, upon returning to the resting position, the first end 81 of the folding guide 5 no longer extends into the folding channel 2, allowing passage of a plunger 30 therethrough.

The folding channel 2 may form part of the bore 40 when disposed in an IOL injector, and thereby allows axial movement of a plunger 30 through the bore 40 to axially advance the folded IOL through the injector body toward the distal end 60 of the nozzle 25, to be delivered into a patient's eye.

In some implementations, for example such as shown in FIG. 4A-4C, the IOL folding guide 5 may have a first end 81 adapted to contact an upper surface of an IOL 70, such as an upper surface 498 of an IOL base 461, and a second end 82 coupled to the IOL folding device housing 99. The folding guide 5 may form a first and a second arm 5a adapted to contact the upper surface 498 of an IOL base 461. Each arm 5a may have a first end 81 and a second end 82, and an inner hook 90a and/or an outer hook 90b may be disposed on the first end 81. The inner hook 90a is adapted to contact an inner edge 471 of an IOL base 461, and the outer hook 90b is adapted to contact an outer edge 472 of a haptic 450, as shown for example in FIG. 3B. Accordingly, the hooks 90a/b are adapted to control the folding of an IOL base 461 as the IOL base 461 is pushed into the folding channel 2. The inner hooks 90a are adapted to stabilize the hollow ring of the base 461 and apply uniform opposing axial outward forces to the inner edge 471 of the IOL base 461, to maintain a more stable center of mass of the IOL base 461. The outer hooks 90b are adapted to stabilize the haptics 450 and keep the haptics 450 close to the base 461 ring's outer edge 475 as the IOL base 461 is folded.

In some implementations of the example IOL folding device shown in FIG. 4A-4C, the inner hooks 90a may be absent and the IOL folding device may be adapted to fold a one-piece IOL 70, or an IOL base 461 having an optic 460 coupled to the IOL base 461. It will be understood that the inner hooks 90b are adapted to contact the inner edges 471 of the hollow ring of the IOL base 461, however they may not be suitable in some implementations for use with a one-piece IOL 70 or a an IOL base 461 having an optic 460 disposed within the base 461.

In some implementations, the IOL base 461 may include proximal and distal notches 473 disposed within the inner edge 471 of the IOL base 461 and the inner hooks 90a may have a size and shape adapted to insert into the notches 473, also providing a more stable contact or coupling between the inner hooks 90a and the IOL base 461. Therefore, the notches 473 have utility for the assembly of the optic 460 onto the base 461, as described above, and also may have synergistic and/or unexpected function allowing contact or coupling of the IOL base 461 with the inner hooks 90a of the folding guide 5.

Figure 5A:
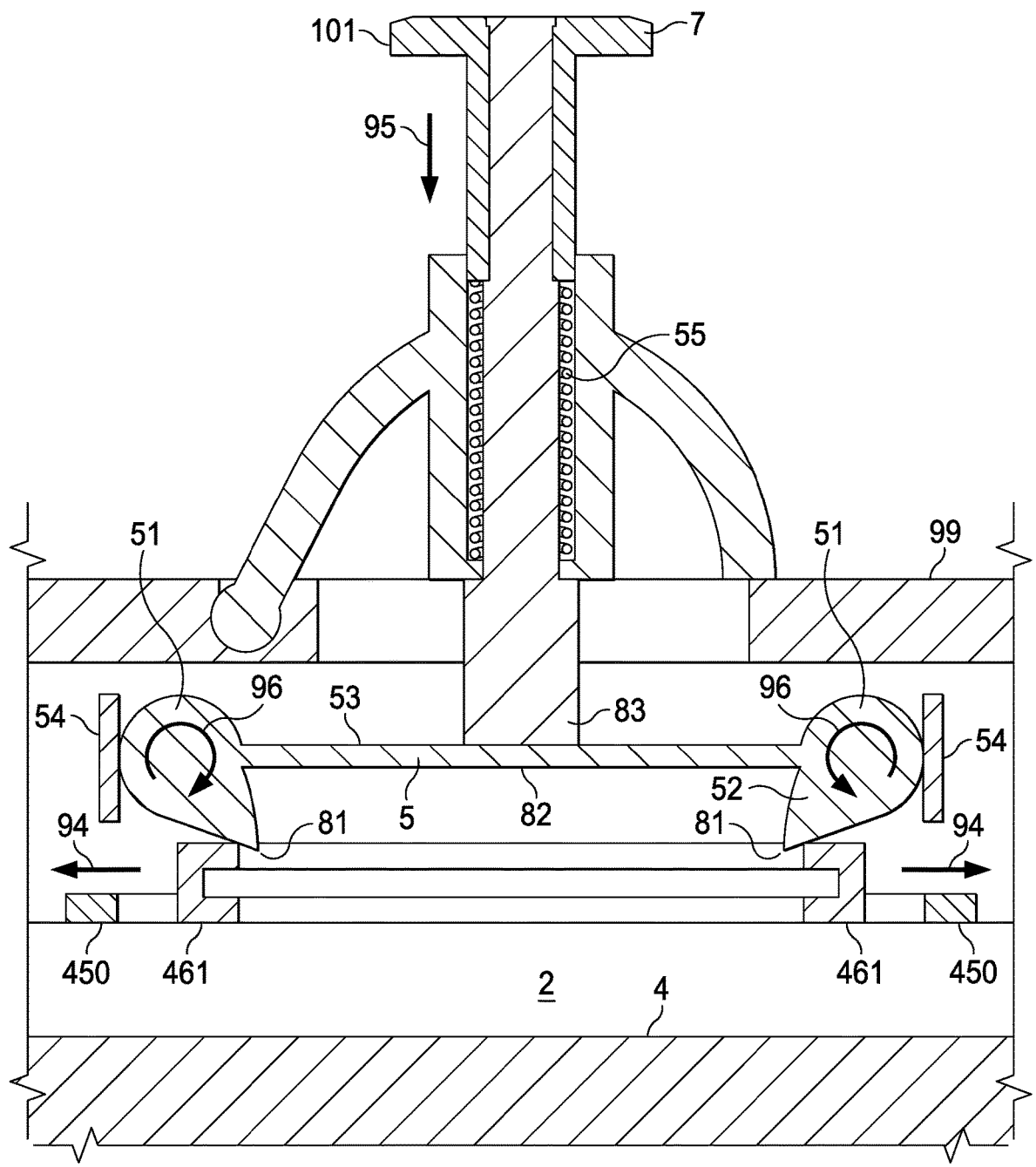
FIG. 5A is a schematic of an example IOL folding device.
Figure 5B:
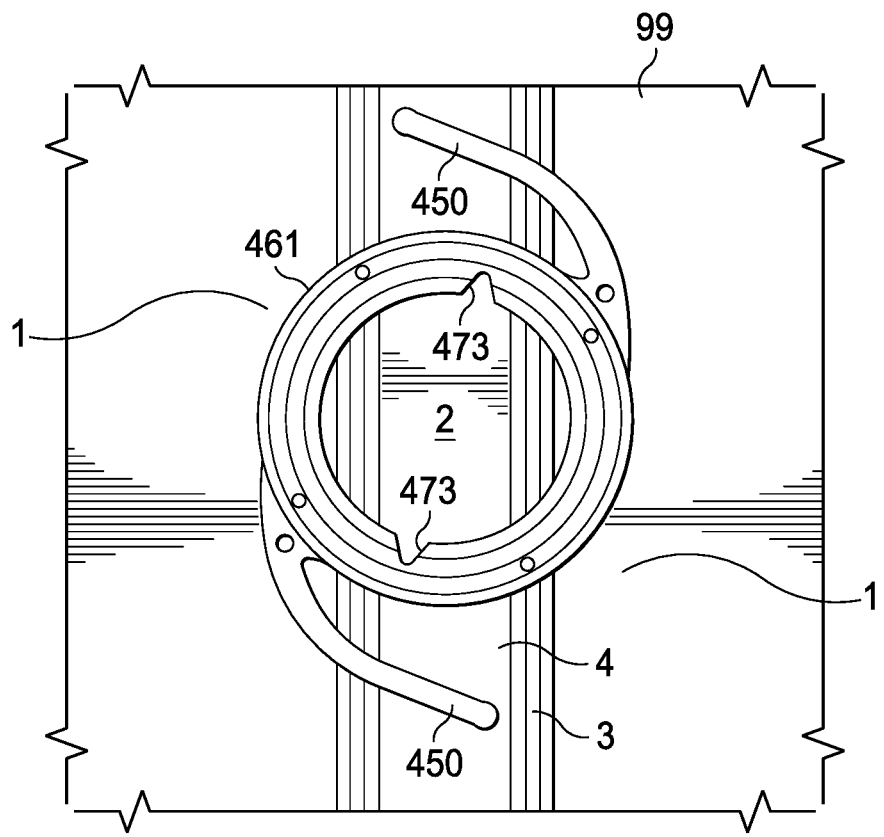
FIG. 5B is another view of the example folding device of FIG. 5A.
Figure 5C:
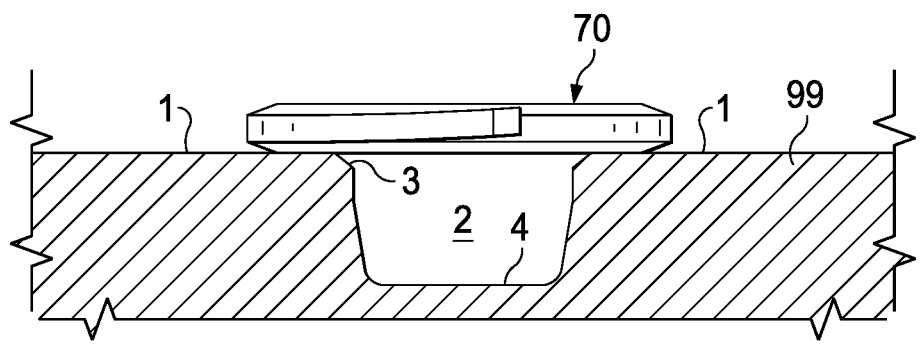
FIG. 5C is another view of the example folding device of FIG. 5A.

FIG. 5A-5C are schematics of another example IOL folding device of the present disclosure. In some implementations, such as in the example shown in FIG. 5A-5C, the IOL folding guide 5 may include a first and a second cam 51, each cam 51 having a wedge 52 extending therefrom and rotatably coupled to a beam 53, for example such as shown in the direction of arrows 96 in FIG. 5A. The cams 51 are rotationally movable along tracks 54, and the wedges 52 adapted to contact an inner edge 471 of an IOL base 461. The IOL folding device may have a user-actuatable button 7 slidably disposed within a first side of the housing 99. The button 7 may have a first end accessible by a user, and the button 7 may be depressible such as in the direction of arrow 95 in FIG. 5A. The button 7 has a second end 83 coupled to the beam 53. The IOL folding device may include a spring 55 having a first end coupled to the button 7 and a second end coupled to the housing 99. The IOL folding device may be configured such that in response to depression of the button 7, the beam 53 is adapted to move from a resting position toward the floor 4 of the IOL folding channel 2, the cams 51 are adapted to rotate along the tracks 54, the wedges 52 are adapted to contact the IOL base 461 and extend into the folding channel 2, pushing the IOL 70 into the IOL folding channel 2 while also axially elongating the IOL base 461. Accordingly, the wedges 52 of the cams 51 are adapted to apply uniform opposing axial outward distal and proximal forces to the inner edge 471 of the IOL base 461, to maintain a more stable center of mass of the IOL base 461 while pushing the IOL into the folding channel 2. The spring 55 is adapted to return the button 7 to the resting position. In response to the button 7 returning to the resting position, the beam 53 of the folding guide 5 returns to the resting position, and in response, the cams 51 of the folding guide 5 are adapted to rotate in a direction opposite to that of arrows 96, as shown in FIG. 5A, such that the cams 5 exit the folding channel 2. Accordingly, upon returning to the resting position, the cams 51 no longer extend into the folding channel 2, allowing passage of the plunger 30 therethrough. After folding the IOL, the IOL folding device is configured such that the folded IOL is retained within the folding channel 2, ready to be axially advanced by the plunger 30.

In some implementations, the IOL base 461 may include proximal and distal notches 473 disposed within the inner edge 471 of the IOL base 461 and the wedges 53 may have a size and shape adapted to insert into the notches 473, also providing a more stable coupling between the wedges 53 and the IOL base 461. Therefore, the notches 473 have utility for the assembly of the optic 460 onto the base 461, as described above, and also may have synergistic and/or unexpected function allowing contact or coupling of the IOL base 461 with the wedges 53 of the folding guide 5.

In some implementations, the IOL folding guide having cams 51 may further include outer hooks coupled to the folding guide 5, such as the outer hooks 90b described above, the outer hooks 90b adapted to contact an outer edge 472 of a haptic 450, thereby configured to stabilize the haptics 450 and keep the haptics 450 close to the base 461 ring's outer edge 475 as the IOL base 461 is folded.

FIG. 6A-6D are schematics of another example IOL folding device of the present disclosure. In some implementations, such as in the example shown in FIG. 6A-6D, the IOL folding guide 5 includes a first and a second flexible arm 5b. Each flexible arm 5b has an inner hook 90a formed on a first end 81 of the flexible arm 5b. The inner hook 90a is adapted to contact an inner edge 471 of an IOL base 461. The IOL folding device may have a user-actuatable button 7 slidably disposed within a first side of the housing 99, the button 7 having a first end depressible by a user, and a second end coupled to a second end 82 of the flexible arms 5b. The IOL folding device may have a spring 55 having a first end coupled to the button 7 and a second end coupled to the housing 99. The IOL folding device may be adapted such that in response to user depression of the button 7, the flexible arms 5b are adapted to move from a resting position above the IOL folding channel 2 toward the floor 4 of the IOL folding channel 2, in a similar manner as that described above for implementations exemplified by the IOL folding device illustrated in FIG. 5A-5C.

Figure 6A:
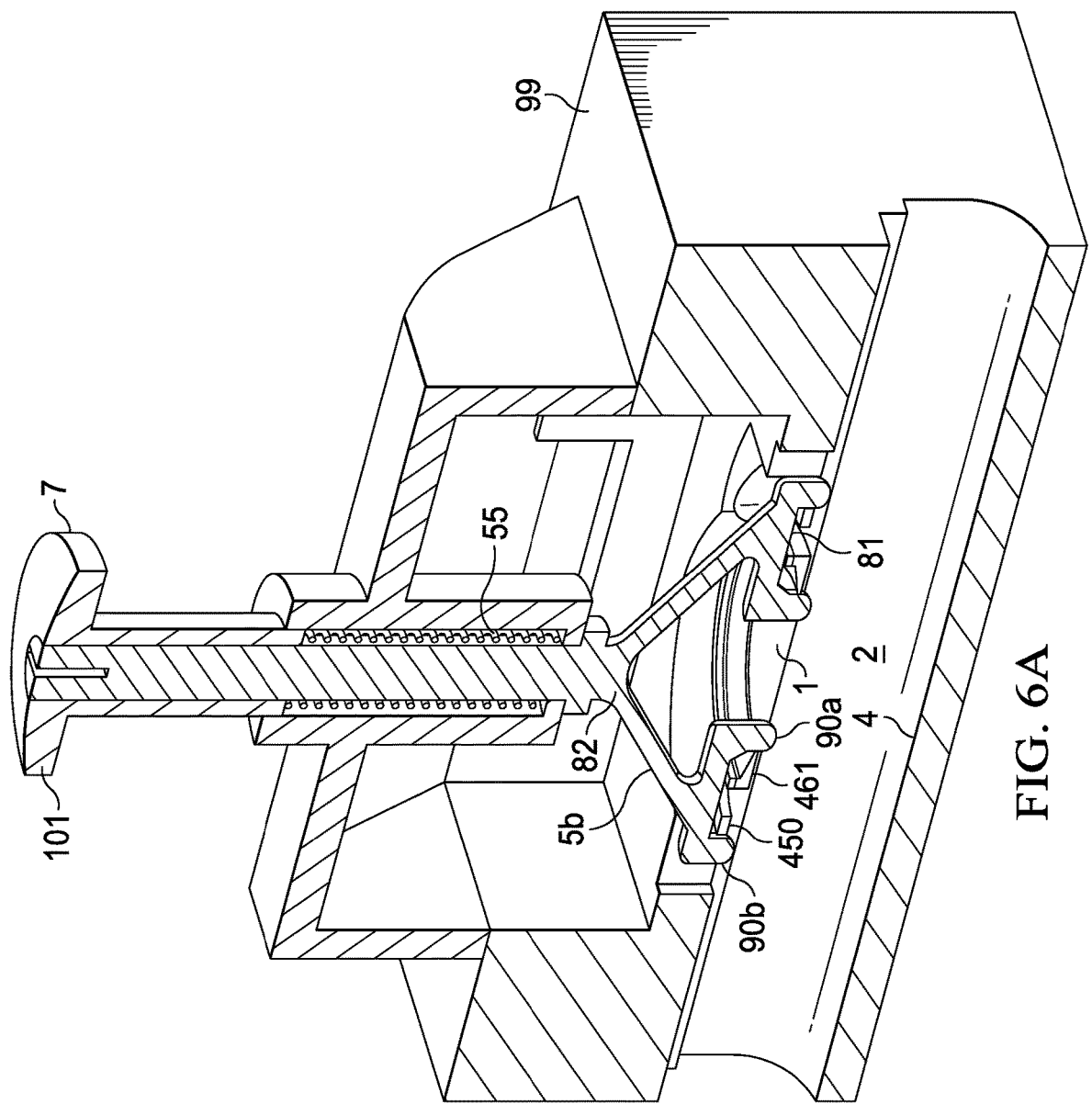
FIG. 6A is a schematic of an example IOL folding device.
Figure 6B:
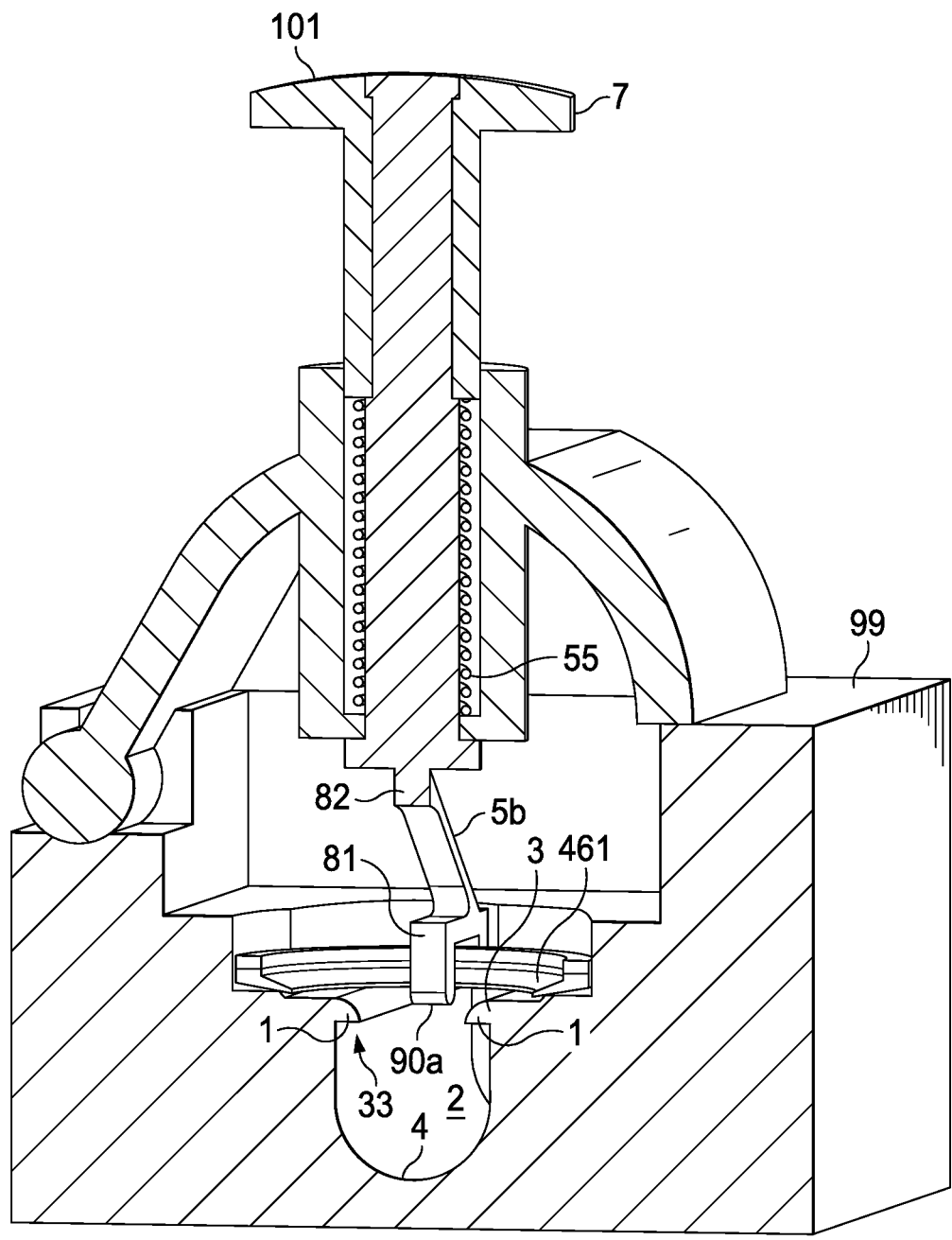
FIG. 6B is another view of the example folding device of FIG. 6A.
Figure 6C:
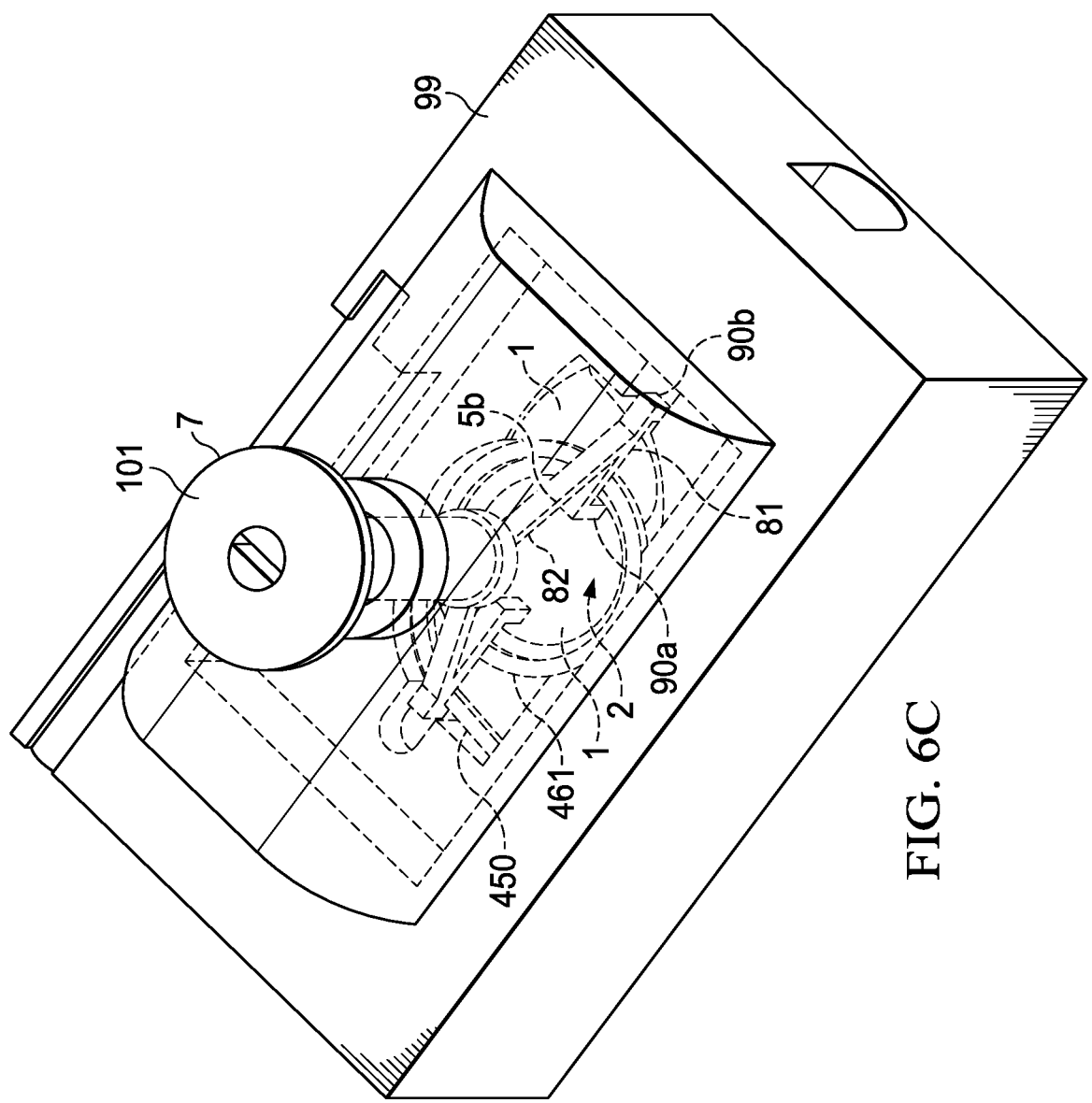
FIG. 6C is another view of the example folding device of FIG. 6A.
Figure 6D:
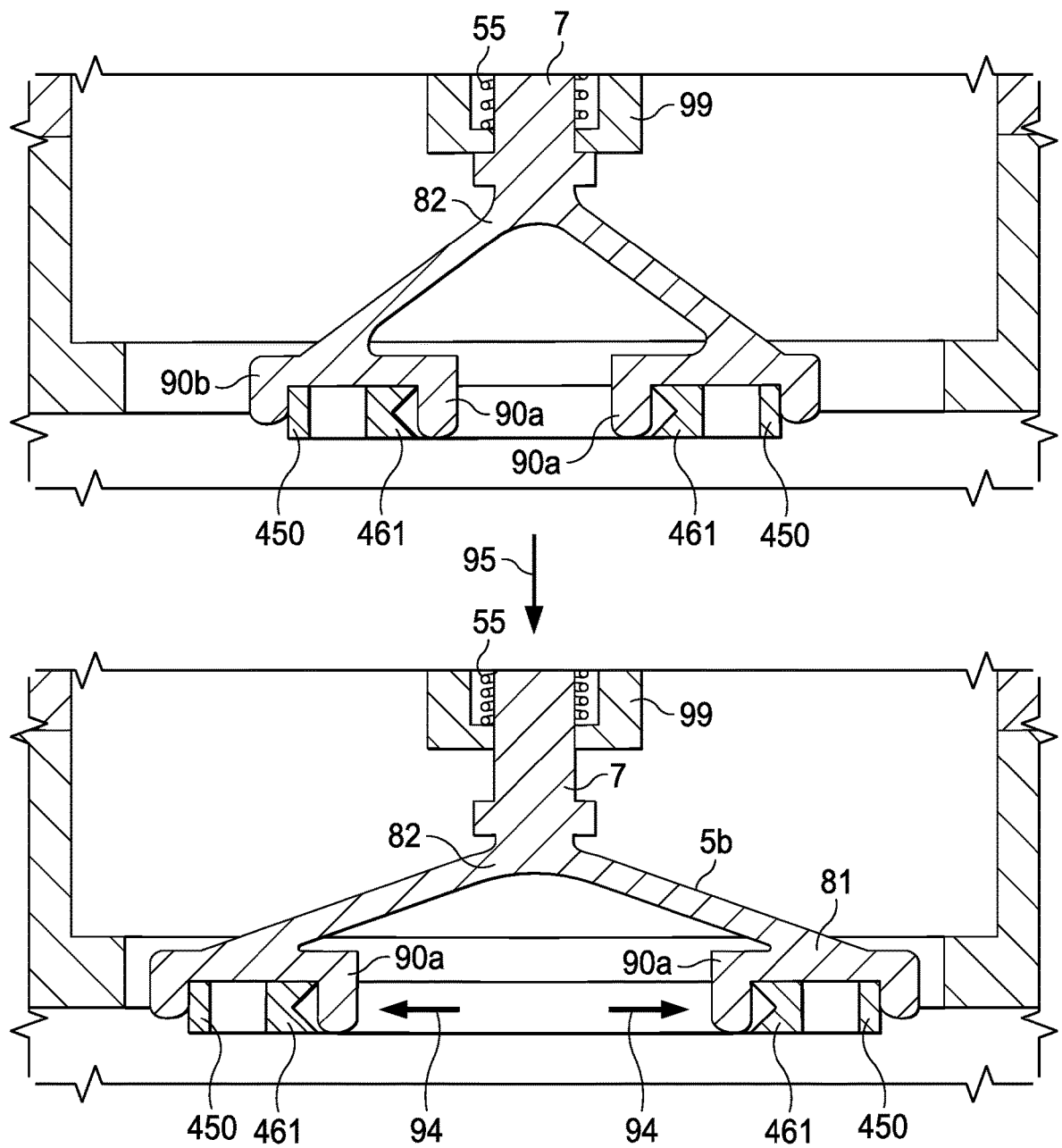
FIG. 6D is a schematic of operation of the example folding device of FIG. 6A.

An unfolded IOL base 461 may exhibit a certain amount of resistance to being pushed into a folding channel 2 and adopting a folded conformation. In response to movement of the flexible arms 5b toward the floor 4 of the IOL folding channel 2, the flexible arms 5b are adapted to flex axially in response to resistance of an unfolded IOL base 461 adopting a folded configuration as the IOL base 461 enters the IOL folding channel 2, such that the first ends 81 of the flexible arms 5b move away from each other, for example as shown in the direction of arrows 94 in FIG. 6D. For example, the upper panel of FIG. 6D shows the flexible arms 5b in an unflexed orientation such as when the folding device is in the unactuated, resting position. The lower panel of FIG. 6D shows the flexible arms 5b in an axially flexed orientation, such as in response to actuation of the folding device by movement of the button 7 in the direction of arrow 95. For example, when the IOL folding device is disposed within an IOL injector, a distally oriented flexible arm 5b is adapted to flex axially toward the distal end 60 of the injector body 20, and a proximally oriented flexible arm 5b is adapted to flex axially toward the proximal end 50 of the injector body 20. For a given IOL base 461, the flexibility of the flexible arms 5b can be optimized such that the flexible arms 5b are able to push the IOL base 461 into the folding channel 2, while also having the ability to flex in response to resistance of the IOL base 461. It will be understood that the type of material, such as flexible plastic, and the weight or thickness thereof, can be selected to optimize the performance of the flexible arms to achieve these desired characteristics.

The inner hooks 90a of an IOL folding device such as shown in FIG. 6A-6D, are adapted to contact the inner edges 471 of the IOL base 461 and axially elongate the IOL base 461, similar to that described above as for the example implementation illustrated in FIG. 4A-4C. Also, similarly as described above, the spring 55 of the example IOL folding device shown in FIG. 6A-6D is adapted to return the button 7 to the resting position, and in response, the flexible arms 5b are adapted to exit the folding channel 2, thereby allowing movement of a plunger 30 of an IOL injector 10 therethrough.

In some implementations, such as shown for example in FIG. 6A-6D, the first end 81 of each of the flexible arms 5b may further include an outer hook 90b adapted to contact an outer edge 472 of a haptic 450. As described above, in response to the axially elongation of the IOL base 461, the outer hook 90b is adapted to keep an inner edge 474 of the haptic 450 in close proximity to or in contact with an outer edge 475 of the IOL base 461.

Also as described above, the IOL base 461 may include proximal and distal notches 473 disposed within the inner edge 471 of the IOL base 461, and the inner hooks 90a of the example IOL folding device of FIG. 6A-6D may be adapted to contact the IOL base 461 at the proximal and distal notches 473.

Figure 7:
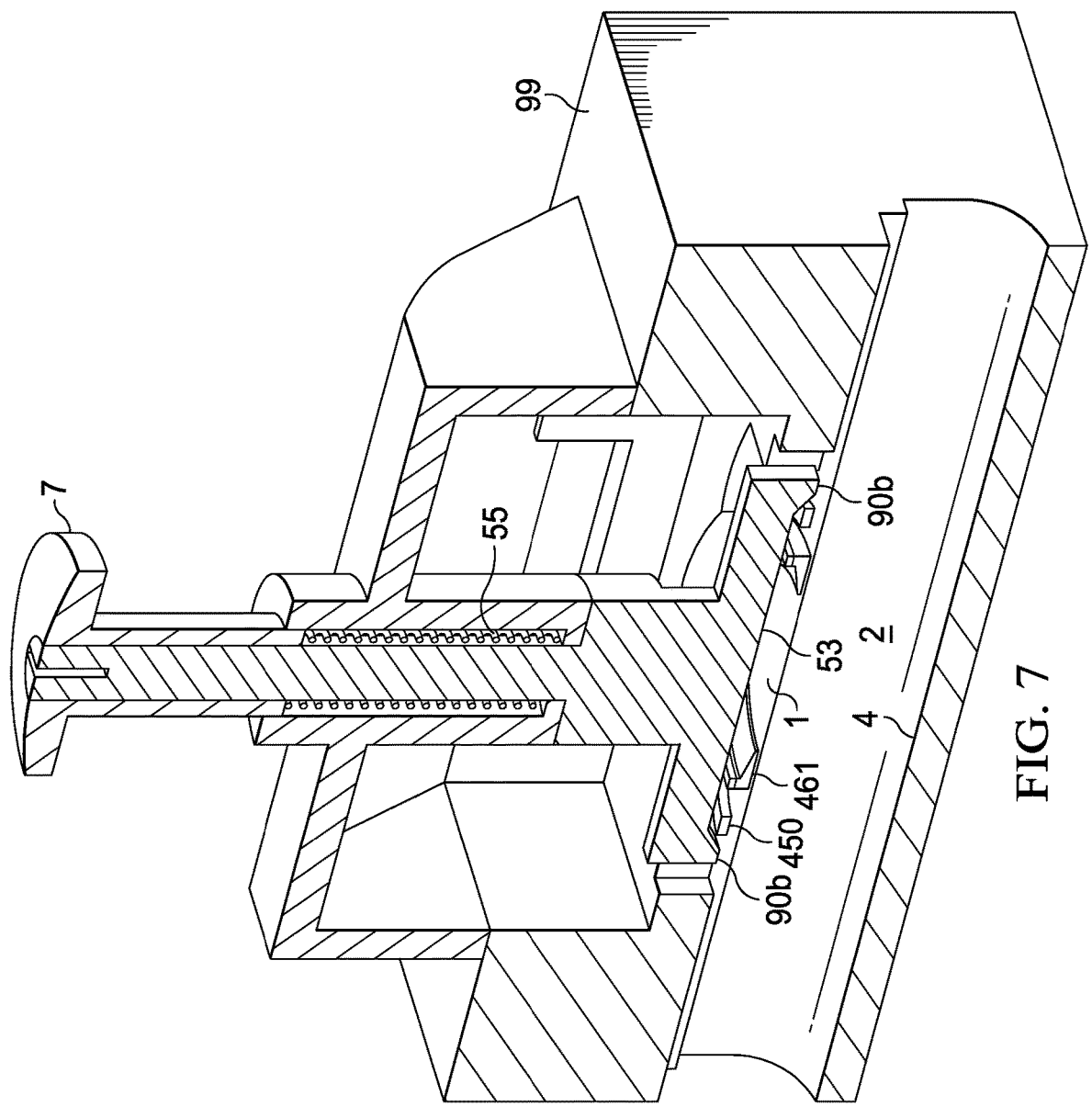
FIG. 7 is a schematic of an example IOL folding device.

FIG. 7 is a schematic of yet another example IOL folding device of the present disclosure. In some implementations, such as in the example shown in FIG. 7, rather than having a pair of actuators adapted to contact the IOL 70, such as, for example a pair of arms 5a, or a pair of cams 51, or a pair of flexible arms 5b, the IOL folding guide 5 may include a single actuator such as a beam 53 adapted to contact an upper surface 498 of an IOL 70. The IOL folding device may include a user-actuatable button 7 slidably disposed within a first side of the housing 99, the button 7 having a first end depressible by a user and a second end coupled to the beam 53. As above, the IOL folding device may further include a spring 55 having a first end coupled to the button 7 and a second end coupled to the housing 99. The IOL injector may be adapted such that, in response to depression of the button 7, the beam 53 is adapted to move from a resting position toward the floor 4 of the IOL folding channel 2, and thereby push the IOL 70 into the IOL folding channel 2, and the spring 55 is adapted to return the button 7 to the resting position.

It will be understood that an IOL folding device having a beam 53 for example as in FIG. 7 is suitable for folding a one-piece IOL 70, or an IOL base 461, or an IOL base 461 having an optic 460 coupled to the IOL base 461.

In some implementations, for example such as shown in FIG. 7, the beam 53 may further include, at a first and second end of the beam 53, an outer hook 90b adapted to contact an outer edge 472 of a haptic 450.

Accordingly, in various implementations, the IOL folding device may be adapted such that, the outer hooks 90b are adapted to push an inner edge 474 of the haptics 450 close to or in contact with an outer edge 475 of the IOL base 461 or close to or in contact with an IOL optic 460, such that the inner edge 474 of the haptics 450 substantially abuts and conforms to a perimeter of the outer edge 475 of the IOL base 461 or the IOL optic 460.

In some implementations, the outer hooks 90b may be adapted to contact the outer edges 472 of the haptics 450 before the beam 53 contacts the upper surface 498 of the ring of the base 461, or before the beam 53 contacts the optic 460 of a one-piece IOL or before the beam 53 contacts the optic 460 coupled to a base 461. Accordingly, the outer hooks 90b may be adapted to push an inner edge 474 of the haptics 450 close to or in contact with an outer edge 475 of the IOL base 461 or close to or in contact with an IOL optic 460 prior to the IOL being pushed into the folding channel 2 and adopting a folded conformation.

After folding the IOL, the IOL folding device is configured such that the folded IOL is retained within the folding channel 2, ready to be axially advanced in the folded configuration by the plunger 30 and does not become unfolded again and/or exit the folding channel before being engaged by the plunger 30 and advanced through the injector body 20. In some implementations, the folding channel 2 may have a surface that provides sufficient friction in contact with the folded IOL so as to prevent the unfolding of the folded IOL and/or exit of the folded IOL from the folding channel 2, when disposed within the folding channel 2.

In some implementations, the IOL folding device may be adapted to separately inject an IOL base 461, an IOL optic 460, or both. In some implementations, the IOL folding device may be adapted to concurrently inject an IOL base 461 and an IOL optic 460.

In use, in various implementations, when the IOL folding device of the present disclosure is disposed within an IOL injector, a user may actuate the lever 6 or the button 7 of the IOL folding device described herein, thereby causing the IOL 70 to adopt a folded configuration. Subsequently, the user may axially slide the plunger 30, such that the plunger tip 220 contacts the folded IOL 70 and thereby advances the IOL 70 through the delivery channel 31 to exit the distal end 60 of the IOL injector 10 to deliver the IOL 70 into an eye of a patient.

Non-limiting examples of IOL injectors that may be adapted according to the present disclosure include those described in U.S. Pat. No. 7,156,854 and U.S. Patent Application Publication No. 2016/0256316, the disclosures of each being incorporated herein by reference in their entireties.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. An intraocular lens (IOL) folding device comprising:
a housing;
a pair of IOL storage shelves disposed within opposite sides of the housing, each IOL storage shelf adapted to support a portion of an unfolded IOL;
an IOL folding channel formed between the IOL storage shelves, each IOL storage shelf coupled to the IOL folding channel by a lip, the IOL folding channel having a longitudinal axis adapted to be aligned with a bore of an IOL injector, and having a bottom surface forming a floor;
an IOL folding guide axially aligned and above the IOL folding channel, the IOL folding guide having a first end adapted to contact an upper surface of an IOL and a second end coupled to the housing or a user-actuatable handle, the user-actuatable handle having a first end accessible to a user and a second end coupled to the IOL folding guide or the IOL folding channel, wherein:
the IOL folding guide comprises a first arm and a second arm, each of the first and second arms having a first end and a second end wherein an inner hook is disposed on the first ends of each of the first and second arms, the inner hooks adapted to contact an inner edge of an IOL base; and
wherein, in response to actuation of a lever or button:
the floor of the IOL folding channel and the IOL folding guide are adapted to be brought closer together, the IOL folding guide thereby configured to push an unfolded IOL into the IOL folding channel and adopt a folded conformation within the IOL folding channel.

2. The IOL folding device of claim 1,
further comprising an outer hook disposed on the first ends of each of the first and second arms, the outer hooks adapted to contact an outer edge of a haptic.

3. The IOL folding device of claim 1, wherein:
the inner hooks are further adapted to contact proximal and distal notches disposed within an inner edge of an IOL base.

4. The IOL folding device of claim 1, wherein:
the lip of each shelf comprises an overhang extending from the shelves partially over the IOL folding channel, wherein the overhang is configured to retain a folded IOL within the IOL folding channel.

5. The IOL folding device of claim 1, wherein the IOL folding device is adapted to be fixedly disposed within or removably disposed within an IOL injector.

6. The IOL folding device of claim 1, wherein the IOL folding device is adapted to separately fold an IOL base, an IOL optic, or both.

7. The IOL folding device of claim 1, wherein the IOL folding device is adapted to concurrently fold an IOL base and an IOL optic.

8. The IOL folding device of claim 1, wherein the floor is configured to be beneath a centroid of an unfolded IOL when the unfolded IOL is positioned on the shelves.

9. An intraocular lens (IOL) folding device, comprising:
a housing;
a pair of IOL storage shelves disposed within opposite sides of the housing, each IOL storage shelf adapted to support a portion of an unfolded IOL;
an IOL folding channel formed between the IOL storage shelves, each IOL storage shelf coupled to the IOL folding channel by a lip, the IOL folding channel having a longitudinal axis adapted to be aligned with a bore of an IOL injector, and having a bottom surface forming a floor;
an IOL folding guide axially aligned and above the IOL folding channel, the IOL folding guide having a first end adapted to contact an upper surface of an IOL and a second end coupled to the housing or a user-actuatable handle, the user-actuatable handle having a first end accessible to a user and a second end coupled to the IOL folding guide or the IOL folding channel, wherein:
the IOL folding guide comprises a first and a second flexible arm, each flexible arm having a first end and a second end, wherein an inner hook is formed on the first ends of each of the first and second flexible arms, the inner hooks adapted to contact an inner edge of an IOL base; and
the IOL folding device further comprising:
a user-actuatable handle comprising a button slidably disposed within a first side of the housing, the button having a first end depressible by a user, and a second end coupled to the second end of the flexible arms; and
a spring having a first end coupled to the button and a second end coupled to the housing;
wherein in response to depression of the button:
the flexible arms are adapted to move from a resting position toward the floor of the IOL folding channel;
the flexible arms are adapted to flex axially in response to resistance of an unfolded IOL base adopting a folded configuration as the IOL base enters the IOL folding channel, such that the first ends of the flexible arms move away from each other;
the inner hooks are adapted to contact the IOL base and axially elongate the IOL base; and
the spring is adapted to return the button to the resting position.

10. The IOL folding device of claim 9, wherein:
the first end of each of the flexible arms further comprises an outer hook adapted to contact an outer edge of a haptic;
wherein in response to the axially elongation of the IOL base:
the outer hook is adapted to keep an inner edge of the haptic in contact with an outer edge of the IOL base.

11. The IOL folding device of claim 9, wherein:
the IOL base comprises proximal and distal notches disposed within the inner edge of the IOL base; and
the inner hooks are adapted to contact the IOL base at the proximal and distal notches.

12. An intraocular lens (IOL) folding device comprising:
a housing;
a pair of IOL storage shelves disposed within opposite sides of the housing, each, IOL storage shelf adapted to support a portion of an unfolded IOL;
an IOL folding channel formed between the IOL storage shelves, each IOL storage shelf coupled to the IOL folding channel by a lip, the IOL folding channel having a longitudinal axis adapted to be aligned with a bore of an IOL injector, and having a bottom surface forming a floor;
an IOL folding guide axially aligned and above the IOL folding channel, the IOL folding guide having a first end adapted to contact an upper surface of an IOL and a second end coupled to the housing or a user-actuatable handle, the user-actuatable handle having a first end accessible to a user and a second end coupled to the IOL folding guide or the IOL folding channel, wherein:
the IOL folding guide comprises a first arm and a second arm, each of the first and second arms having a first end and a second end, wherein an outer hook is disposed on the first ends of each of the first and second arms, the outer hooks adapted to contact an outer edge of haptic; and
wherein, in response to actuation of a lever or button:
the floor of the IOL folding channel and the IOL folding guide are adapted to be brought closer together, the IOL folding guide thereby configured to push an unfolded IOL into the folding channel and adopt a folded conformation within the IOL folding channel.

* * * * *